United States Patent [19]
Namery

[11] 3,974,681
[45] Aug. 17, 1976

[54] ULTRASONIC BUBBLE DETECTOR

[76] Inventor: Jerry Namery, 21 Larkspur Way, Natick, Mass. 01760

[22] Filed: Oct. 23, 1973

[21] Appl. No.: 408,269

[52] U.S. Cl. ................................ 73/67.5 R; 73/19; 73/71.5 US; 128/2 V; 128/2.05 Z
[51] Int. Cl.$^2$ ........................................ G01N 29/02
[58] Field of Search .................. 73/67 SR, 61 R, 24, 73/67.6, 67.7, 67.8 R, 19, 67.9, 53, 71.5 US, 104 A; 128/2 V, 2.05 Z, 2.05 R, 2.05 F; 310/8.2, 9.1

[56] References Cited
UNITED STATES PATENTS

| | | |
|---|---|---|
| 2,448,352 | 8/1948 | Carlin ........................ 73/71.5 US X |
| 2,573,390 | 10/1951 | Blanchard ..................... 73/67.5 R X |
| 2,724,107 | 11/1955 | Born ........................... 73/67.8 UX |
| 3,283,562 | 11/1966 | Heisig et al. ..................... 73/19 |
| 3,486,370 | 11/1969 | Chedeville et al. ................. 73/67.6 |
| 3,640,271 | 2/1972 | Horton ....................... 128/2.05 F X |
| 3,663,842 | 5/1972 | Miller ............................ 73/67.8 R |
| 3,689,783 | 9/1972 | Williams ......................... 310/9.1 X |
| 3,794,866 | 2/1974 | McElroy et al. ............. 73/67.5 R X |

OTHER PUBLICATIONS

Manley, Ultrasonics, "Ultrasonic Detection of Gas Bubbles in Blood," Apr. 1969, pp. 102–105.
Mole et al., Journal of the Acoustical Society of America, "Scattering of Sound by Air Bubbles in Water," Sept. 1972, pp. 837–842.
Nishi, Ultrasonics, "Ultrasonic Detection of Bubbles with Doppler Flow Transducers," July 1972, pp. 173–179.

*Primary Examiner*—Richard C. Queisser
*Assistant Examiner*—Stephen A. Kreitman
*Attorney, Agent, or Firm*—Wolf, Greenfield & Sacks

[57] ABSTRACT

The mode of operation is by ultrasonic through-transmission, and the detector is preferably employed for detecting air bubbles in intravenous feeding tubes to prevent air embolism. Transmission of sound from the transmitter, via the sensor head, to the receiver of the detector is dependent upon the existence of a fluid within the tubing. Acoustic losses, operating frequency, and the distance between transmitter and receiver are optimized to permit constructive-interference of energy transmitted to and reflected from the receiver, resulting in a partial standing wave as in a resonant cavity. If an air bubble passes through the sensor head a large acoustic discontinuity occurs, causing ultrasound to scatter and reflect from its normal path. These losses allow little ultrasonic energy to couple to the receiver. The sensor head includes oppositely and spacedly disposed cylindrical sound pipe segments having facing tubing accommodating recesses, and respectively connecting to the transmitter and receiver. Sound pipe segments have a markedly higher refractive index in comparison with the feeding tubing and its liquid contents causing ultrasound energy to focus towards the center of the feeding tube, thereby yielding greatest sensitivity to transmission losses through the fluid within the feeding tube.

19 Claims, 10 Drawing Figures

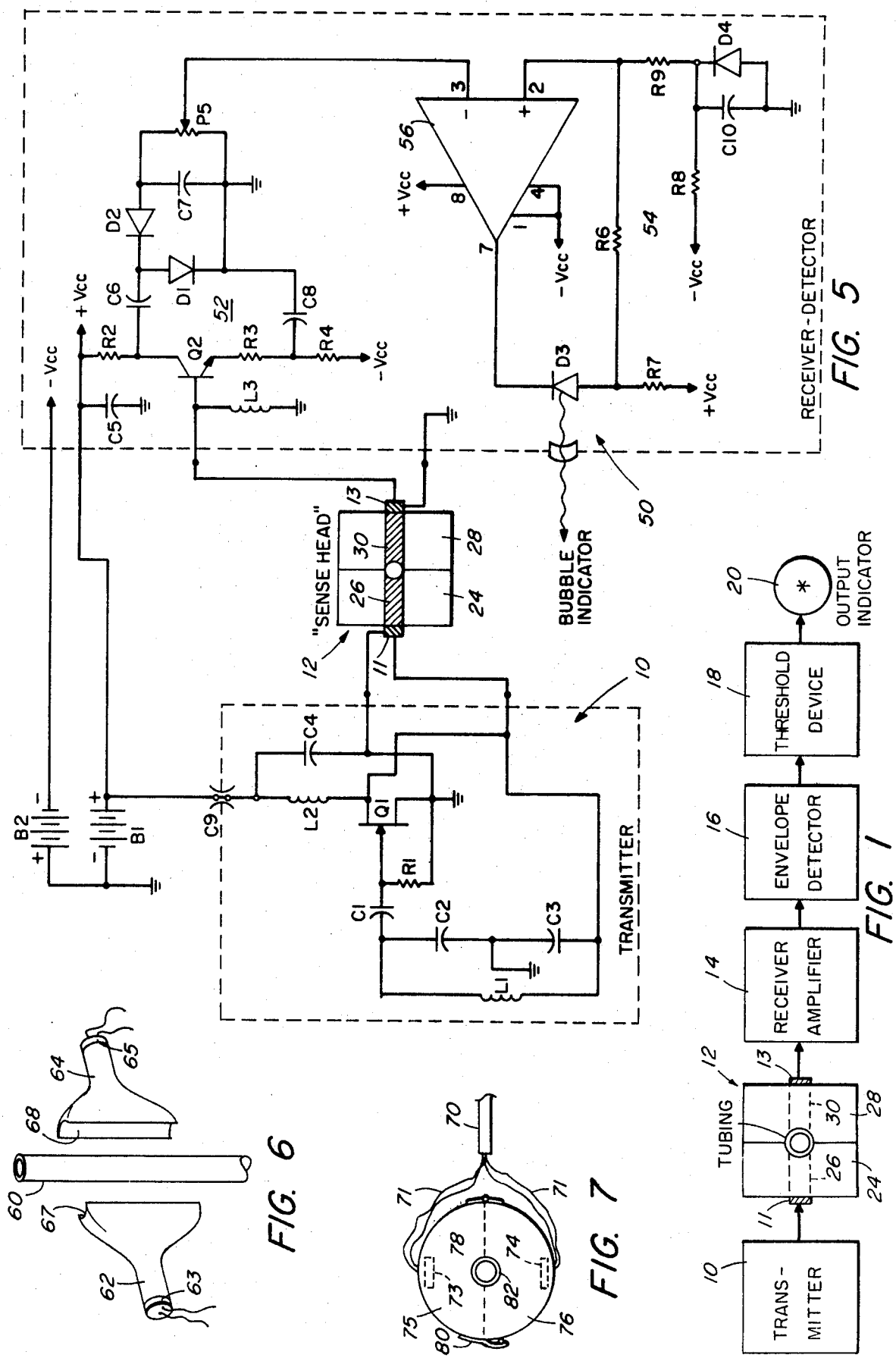

ULTRASONIC BUBBLE DETECTOR

FIELD OF THE INVENTION

The present invention relates in general to an apparatus or device for detecting gas or gas bubbles traveling in a feeding tube, such as an IV tube. More particularly, this invention pertains to an ultrasonic bubble detector using through-transmission detection.

BACKGROUND OF THE INVENTION

The problem of preventing air embolism (obstruction of a blood vessel by an air bubble) during intravenous feeding has received mixed attention by the medical profession. The quantity of gas the circulatory system may sustain without hazard is difficult to estimate; recently, the figure of 40 to 50 cc (cubic centimeter) has been generally accepted as definitely hazardous to life. This amount is not small, so that at present, gravity-fed, intravenous feeding apparatus is almost adequate in impeding air intake should the IV bottle empty; provided the attendant nurse and/or patient is alert. Nevertheless, cases have been reported of deaths caused by air embolism through negligence.

Presently, the problem of detecting air bubbles in feeding tubes to prevent air embolism is receiving attention by engineers and doctors who are developing automated intravenous techniques: for treatment of hemodialysis patients, for precise application of fluids and medication in the operating room, and for replacing gravity-fed IV devices in the recovery ward. With these automatically-controlled active IV pumps, the problem of exceeding the 40-to-50 cc air tolerance level becomes more acute. The new techniques employ local or remote (computer) programming of fluid flow. The purpose of the bubble detector is then to stop the flow by mechanically clamping the feeding tube, to turn off the pump, to warn the attendant nurse, and to give a visual or audio indication of the precautionary state.

Possible methods of bubble detection in tubes are: (1) photoelectric, (2) electronic, (3) ultrasonic, and (4) other. The photoelectric technique has been utilized in a commercial bubble detector for dialysis tubing (by Vital Assists, Inc.) - but it is perhaps the most unreliable method: it is plagued by a low detection threshold level between, say, clear saline and air, and requires adjustments for fluids of different opacities.

The electronic method is based on the difference in electrical impedance between fluid and air. The real part of the impedance, that is the D.C. resistance, can only be measured by electrode contact within the fluid, and it obviously will depend on the fluid's ionic concentration. The purely imaginary part of the impedance, that is the capacitance, differs significantly (80X) between water and air, but sophisticated laboratory equipment is required to measure the slight capacitance changes caused by a small bubble (i.e., 1 mm in diameter). This parameter can be measured with plates outside the intravenous tube, which are connected to an AC-impedance bridge, for example. The bridge must be carefully balanced to a null when fluid is present in the vessel. This device has been reported in the literature by B. C. Taylor et al. "An Instrument for the Prevention of Air Embolism in Hemodialysis Patients," 25th American Conference of Engineers in Medicine and Biology Proceedings, 1972, P. 175. This method of detection is prone to errors due to inherent low threshold detection (i.e., detection of approximately a 1 picofarad capacitance change), and still requires complex analog hardware costing hundreds of dollars in a stand-alone unit. Also, frequent calibration is probably necessary using this technique.

The ultrasonic approach is based on the large acoustic impedance mismatch between liquid and air, and the relatively insignificant acoustic impedance difference between water-based fluids of different concentrations, opacities, and colors. Some researchers have used ultrasonics for bubble detection. For example, the detection of small bubbles in the blood vessels of divers with decompression sickness has been reported by G. J. Rubissow and R. S. Mackay, "Ultrasonic Imaging of Bubbles in Decompression Sickness," Ultrasonics, Vol. 9, No. 4 (1971), p. 225; R. Y. Nishi, "Ultrasonic Detection of Bubbles with Doppler Flow Transducers," Ultrasonics, Vol. 10, No. 4, p. 173 (1972); A. Evans and D. N. Walder, "Detection of Circulating Bubbles in the Intact Mammal," Ultrasonics, Vol. 8, No. 4, p. 216 (1970).

One prior art method using ultrasound for detecting bubbles in a small tube is to immerse it in a water tank lined with a sonic absorbent (i.e., anechoic chamber for ultrasound). The tube is then inspected with an "ultrasonoscope," a device used in non-destructive testing. It generates ultrasonic bursts, then detects backscattered echoes in a sonar fashion, displaying them on a cathode-ray tube (amplitude vs. time). The detection of large echoes from the area of the tube indicates the presence of air. To implement such a system requires elaborate, bulky equipment. Engineers working in the field have come to regard the ultrasonic approach as the most cumbersome and hence the least attractive of the modalities applicable to this problem.

One report in the literature, "Ultrasonic Detection of Gas Bubbles in Blood," by D. M. J. P. Manley, Ultrasonics, April, 1969, pertains to an ultrasonic through-transmission bubble detector for fluids in feeding tubes. the prototype device reported consists of a dual-section chamber, for intake and outlet of fluid, and a small orifice connecting the sections designed to control fluid flow. Ultrasonic transmitter and receiver crystals are coupled appropriately to opposing sides of the lower and upper chamber, respectively, so that ultrasonic energy to the receiver must flow through the orifice in the same direction as fluids flow.

The impracticality of the device is apparent when considering the elaborate and bulky equipment required, the poor performance achieved, and the fact that the device is invasive to the tubing, i.e., requiring liquid to actually flow through the detector chambers. Manley used an operating frequency of 43 KHZ, since at the higher frequencies, the effects of air bubbles on the strength of the received signal were not so prominent. At this low ultrasonic frequency, the wavelength is large (37 mm in water), requiring large transducers, large transmitter amplifier power, and a long path length for the orifice. The actual device as described used 2 inches thick, 2 inches diameter transducers as transmitter and receiver, a stable frequency oscillator and a power amplifier to drive the transmit transducer, and at the receiver a low-frequency tuned-amplifier, detector, and postamplifier. The dimensions of the chamber and orifice are not given, but they are shown as large compared to an IV feeding tube (typically around 5 mm). Manley reports getting a 9–10 db signal reduction by the simultaneous presence of 30 bubbles, around 1 mm each, in the path of the transducers. Since the bubbles are many times smaller than the ultrasonic wavelength, the mechanism of attenuation is acoustic absorption, probably due to thermal compression at the bubble sites. Because this kind of attenuation is small, only the effect of many bubbles and long path length (at least 3 or 4 wavelengths in water) are required. other deficiencies include: (1) due to the low operating frequency external vibrations of the chamber produce marked effects [.e., false alarms]. Isolation is needed for experiments, as anti-vibration mounts are essential for these chambers. (2) The relatively high energy at low frequencies is known to be damaging to blood cells, especially those streaming at the transmitter transducer.

other approaches may be based on the differential thermal conductivity properties between air and water, although there does not appear to be any work reported in the literature using this technique.

OBJECTS OF THE INVENTION

Accordingly, one object of the present invention is to provide an ultrasonic bubble detector wherein the mode of operation is by ultrasonic through-transmission.

Another object of the present invention is to provide an improved ultrasonic bubble detector preferably for detecting air bubbles in an intravenous feeding tube and wherein the modality employed to sense air bubbles possesses a high detection threshold between gas and fluid, yet which preferably does not differentiate between the fluids of different color, opacity, ionic concentration, etc. With such a device the probability of errors is minimized. A further object of the present invention is to provide a bubble detector device including a remote bubble sensor which can be placed very close to the patient.

Still another object of the present invention is to provide a sensor for air bubbles that is easily applied to an existing intravenous feeding tube, that is non-intrusive with respect to sterile tubing or the fluid therein, that presents no electrical, mechanical, or chemical hazards to the patient, and does not damage or modify the fluid therein.

Still a further object of the present invention is to provide a bubble detector device in accordance with the preceeding objects and that is relatively simple and rugged in construction, low in cost, reliable, that requires little or no adjustment or periodic calibration, is immune to vibration, and that can be simply tested to check whether it is operating properly.

Additional specific objects of the present invention are to provide a detector that is preferably battery operated, that consumes a very small standby power thereby permitting the device to be portable, that is readily adaptable to accommodate tubing of widely-differing diameters, and that can be initially adjusted by the manufacturer to detect an air bubble of a predetermined size or larger.

SUMMARY OF THE INVENTION

To accomplish the foregoing and other objects of this invention, there is provided an ultrasonic bubble detector for use with a tube such as an intravenous feeding tube carrying a liquid. The detector generally comprises transmitting means for establishing an ultrasonic signal, a sensor head to which the ultrasonic signal is coupled and a receiver means for receiving the ultrasonic signal including means for establishing a hazardous condition when the received signal falls below a predetermined threshold level. The attenuation of the signal is caused by the passage of an air bubble or bubbles across the path of the sensor head which is disposed about the feeding tube. The transmitting means for establishing an ultrasonic signal may be an electronic oscillator coupled to a transmitter transducer. The sensor head preferably includes a pair of sound pipes each contacting the tube and each embedded in a sound absorbent means.

The facing surfaces of the two sound pipes are preferably configured to receive the feeding tube and are preferably provided with a gap therebetween. The ultrasonic signal is transmitted through one of the sound pipes, the feeding tube including the liquid contained therein, to the second sound pipe which couples to a receiver-detector circuit that is responsive to the received signal falling below a predetermined threshold thereby indicative of the presence of one or more air bubbles in the tube.

In accordance with one aspect of the present invention the sound pipes are each cylindrical in shape and have a semi-circular cavity for receiving the feeding tube. In another embodiment the sound pipes have a fanned-out end contacting the feed tube and in this embodiment primarily only larger bubbles are detected.

BRIEF DESCRIPTION OF THE DRAWINGS

Numerous other objects, features and advantages of the invention will now become apparent upon a reading of the following detailed description taken in conjunction with the accompanying drawings, in which:

FIG. 1 is a block diagram of the device of the present invention;

FIG. 5 is a circuit diagram of the detector of this invention including transmitter and receiver circuitry;

FIG. 6 is an alternate embodiment of the sound pipes;

FIG. 7 shows an arrangement for a sensor head which can be remotely disposed.

DETAILED DESCRIPTION

Figure 8:
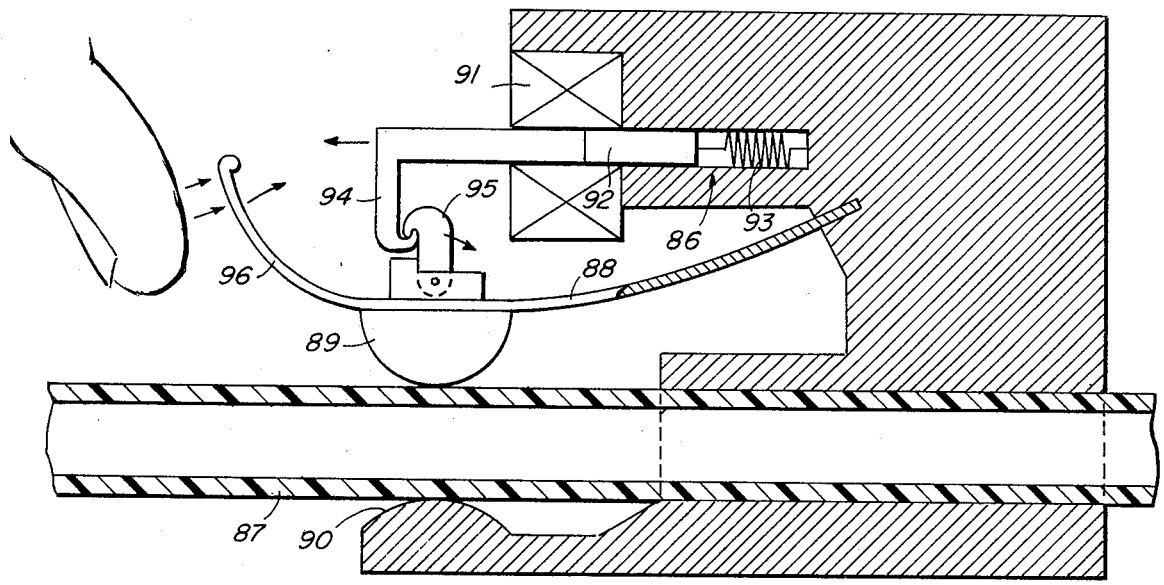
FIG. 8 shows a partially cross-sectional view of a shut-off mechanism useable with the device of this invention.

The bubble detector of the present invention is constructed based upon an ultrasonic through-transmission principle. The device of the present invention is characterized by a high threshold and hence a small error probability. There is at least 30 to 1, typically 80 to 1, reduction in signal when a small bubble on the order of one millimeter in diameter is present in the tube when it is filled with any fluid. The sensor head of this invention is constructed in the form of a sonic resonator cavity and the reduction in signal referred to herein is facilitated by (1) reflection of sound back to transmitter transducer, (2) attenuation of the through-transmission of sound, (3) the scattering of the sound from a straight path causing geometrical attenuation, and (4) the change in resonance by altering the sonic path length when a bubble is present.

The device of the present invention is also relatively simple in construction and can be manufactured at a relatively low cost. There are no special adjustments or construction techniques that are necessary and there is no requirement for calibrating the device in the field. The device is small, portable and is preferably battery operated with very little battery drain. The sensor head is rugged, can be made with transmitter and receiver electronics embedded in a self-contained unit, can be easily changed for different diameter tubes, can be easily disposed about the tubing at any desireable location without impeding fluid flow and is preferably primarily constructed of plastic and essentially completely electrically safe. It is relatively simple to test the performance of the device simply by loosening the coupling of the sensor head to the tube. When this is loosened a bubble detection should occur which is not actually caused by a bubble but by the losse coupling of the sensor head.

FIG. 1 shows a block diagram of the device of the present invention including a transmitter 10, a sensor head 12, a receiver amplifier 14, an envelope detector 16, a threshold detector 18, and an output indicator 20. All of the blocks shown in FIG. 1, with the exception of the sensor head, are disclosed in more detail in the circuit diagram of FIG. 5. The transmitter 10 may include a sinusoidal oscillator that drives a transmitter transducer 11 which forms a part of the sensor head in the disclosed embodiment. The details of the transmitter transducer are discussed in more detail hereinafter with reference to FIGS. 2—4.

In FIG. 1 the sensor head 12 is represented by sound absorbent cubes 24 and 28 having respective sound pipes 26 and 30 imbedded therein. A receiver transducer 13 is disposed for receiving the soundwave generated from the transmitting transducer at one end of sound pipe 30 and is coupled to receiver amplifier 14. The receiver transducer 13 is excited by the local vibrations, and generates a sinusoidal electrical signal, which is amplified by amplifier 14, passed to envelope detector 16 and from there to a threshold detector or comparator circuit 18 for detecting a reduction in the sensed signal. When this occurs the output indicator 20 is activated causing a visual or audible alarm and preferably an interruption of the feeding of fluid in the tube.

FIG. 1 shows in a general manner the components of the system of the present invention. For a more thorough understanding of each of these components the sensor head is disclosed in more detail in FIGS. 2–4 and the circuitry associated therewith is disclosed in detail in FIG. 5. There are a number of important features associated with transmitter 10. For example, one side of the disc transducer 11 is grounded, making it electrically safe. The other connection can be encapsulated in epoxy. Excellent frequency stability is achieved since the reactance of the transducer is frequency-dependent (as in a quartz crystal) and the oscillator is thus locked at a very narrow frequency band when driven near resonance. As a result, there is little frequency shift or amplitude change with temperature or because of poor component tolerances, and there is little frequency shift as the operating voltage is dropped from 25 volts, for example, down to say 3 volts.

Another important characteristic of the transmitter 10 is that there is an effective doubling of the output signal. If the voltage at the transducer 11 is measured its peak-to-peak value is approximately twice the operating voltage supplied by battery B1. This assures a hefty signal at the receiver end, even if the operating voltage from battry B1 is dropped to a low value of say 1.5 volts. Capacitors C4 and C5 of transmitter 10 are used to assure good AC ground and may be unnecessary if battery B1 is disposed close to transmitter-transducer 11.

The transmitter 10 is shown in detail in FIG. 5 and comprises a junction-field-effect transistor Q1, capacitors C1–C4 and inductors L1 and L2. Transmitter 10 receives its power from battery B1 by way of connector C9 to inductor L2 and capacitor C4. Transmitter 10 is of the Colpitts oscillator type. The resonant tank circuit is comprised of coil L1, and capacitor C3 in parallel with the transducer capacitors, both of which are in series with capacitor C2. The embodiment shown in FIG. 5 is a split capacitor oscillator which permits the use of relatively smaller inductors than is the case in the tapped-coil embodiment of a Colpitts oscillator. Also, this design permits grounding of one side of capacitors C2 and C3 which provides improved frequency stability. The transmitter transducer 11 electrically functions as a capacitor as it has spaced metalic plates and is in parallel with capacitor C3 of the oscillator. The values of inductor L1 and capacitors C2 and C3 are preselected to provide the proper operating frequency which is determined by the thickness of the transducer used. In one case this frequency was selected at one megahertz (1MHZ) representing a wavelength in water of 1.5 mm. The operating frequency is governed by the relationship:

where
$$f = (1/2\pi \sqrt{L/C})$$

$$C = \frac{(C3 + C_t) C2}{C3 + C_t + C2}$$

where $C_t$ = total capacitance of the transmitter-transducer.

Figure 2:
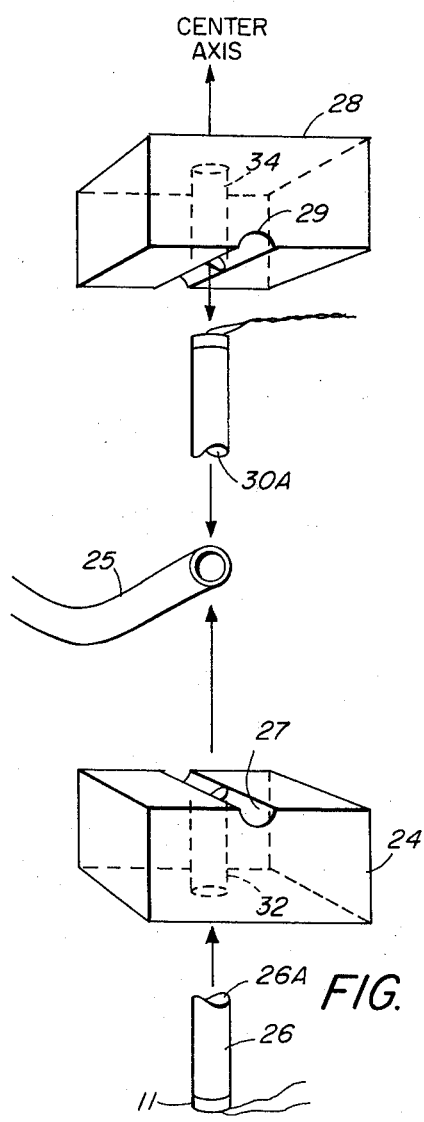
FIG. 2 is an exploded perspective view of the sensor head of the present invention.

FIG. 2 shows an exploded view of the sensor head of the present invention shown somewhat schematically in FIGS. 1 and 5. As previously indicated, the sensor head comprises sound pipes 26 and 30 having transducers 11 and 13 respectively associated therewith and imbedded respectively in sound absorbent members 24 and 28. FIG. 2 also shows a segment of the feed tube 25 which fits within facing semi-cylindrical recesses or channels 27 and 29 of sound absorbent members 24 and 28, respectively. The members 24 and 28 are also provided with cylindrical through passages 32 and 34 associated with members 24 and 28, respectively for receiving corresponding sound pipes 26 and 30. The facing ends of sound pipes 26 and 30 are also provided with arcuate channels 26A and 30A.

Figure 3:
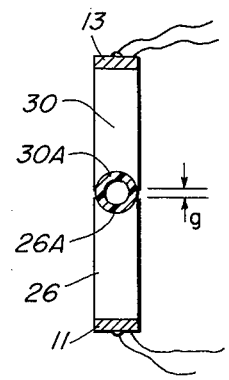
FIG. 3 shows the sound pipes disposed contacting the feed tube.

Referring now to FIG. 3 it is noted that the channels 26A and 30A are held about the tube 25 when the assembly of the sensor head is in its secured together position. The sound-pipes 26 and 30 are preferably glued into their associated sound absorbent members and a suitable means is provided for attaching these two members together about the feed tube 25. It is noted in FIG. 3 that a gap is provided between the channel-defining ends of the sound pipes.

Figure 4:
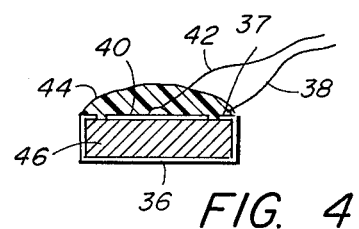
FIG. 4 is a cross-sectional view of one of the transducers shown in FIG. 2.

FIG. 4 shows a cross-sectional view of one of the transducers 11 or 13. These transducers may be of conventional design and in the disclosed arrangement are of coaxial construction including a peripheral gold electrode 36 having a solder joint 37 to which a silver wire 38 is attached. The transducer also includes a coaxially arranged electrode 40 having the hot wire 42 affixed thereto. An epoxy 44 covers this electrode 40. The transducer is primarily constructed of a dielectric material indicated by the reference number 46 and identified in the art as a PZT-5 ferro-electric crystal. The transducer is operable in the compressional mode at a frequency of 1 megahertz. The coaxial construction makes it easier to solder silver wires especially to the outer gold electrode. Since the Curie points of the ferro-electric crystal are low, soldering must generally be quick and with a low heat iron.

The diameter of the sound pipes 26 and 30 should be approximately equal to the diameter of the transducers. This diameter should also be approximately equal to the diameter of the feeding tube 25. However, for some applications where too small a transducer is impractical, it is possible to use a larger diameter sound pipe and associated transducer.

As previously indicated, there is a gap shown in FIG. 3 between the sound pipes 26 and 30. This gap is most easily formed by making the channels 26A and 30A smaller in diameter than the outer diameter of the feed tube 25. This gap should also be present when the sensor head is secured about the feed tube. Obviously, the sensor should not be secured too tightly to prevent the feeding of fluid through the tube. By providing the gap $g$ it is insured that the sonic path will pass through the tube and not be shorted out by contact between the two sound pipes.

In accordance with the present invention it is also preferable to construct the sensor head in two symmetrical halves as shown in FIG. 2. This simplifies the production of the head wherein either transducer can be used as transmitter or receiver. The sound pipes may be constructed of a material with negligible ultrasonic attenuation whose acoustic impedance is close to that of water, but having as low a refractive index from water as possible (acoustic refractive index $n$ = ratio of sound velocity). Suitable materials are metals, such as aluminum, brass, etc. The sound absorbent cube, which may also be configured as a sphere or oval, may be made of any high ultrasonic attenuation material such as polyethylene or teflon. In the preferred embodiment the sound pipes were constructed of aluminum and the sound absorbent members 24 and 28 were constructed of teflon in water to sound velocity in sound pipes.

Figure 9:
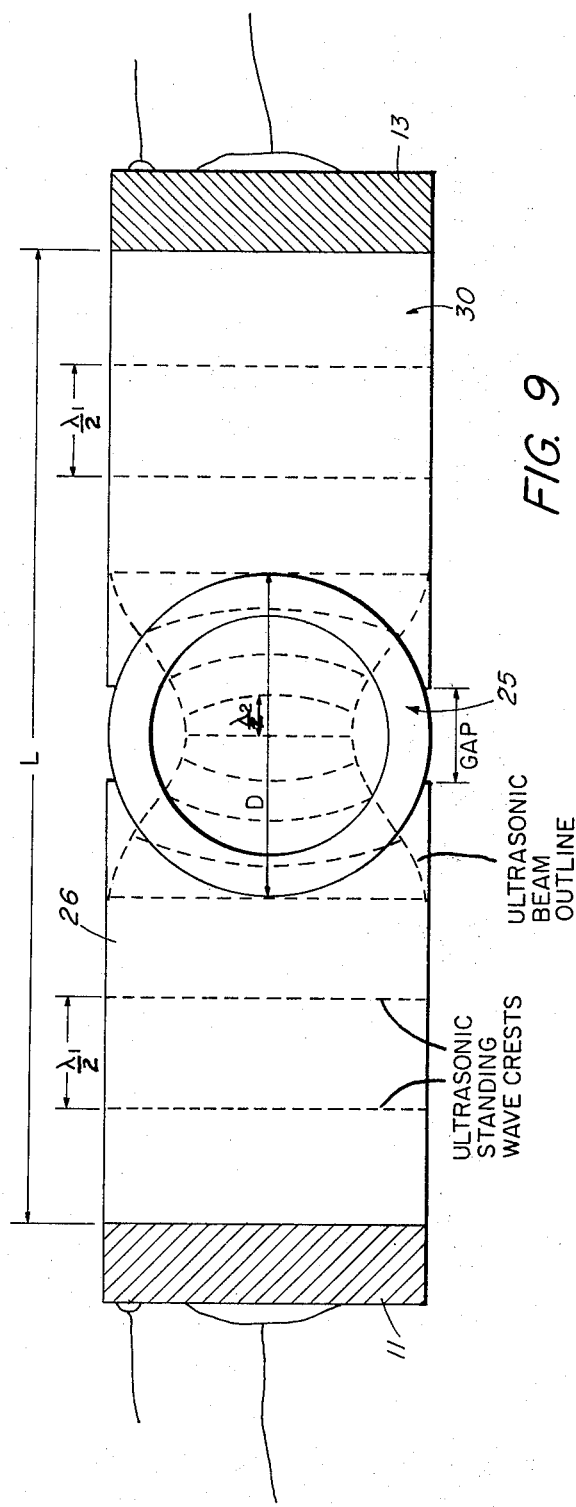
FIG. 9 shows the standing wave pattern and beam outline in the transmitter-receiver cavity.

As previously indicated the attenuation of the sound signal when a bubble is detected is caused by at least four phenomenon one of which is the change in the sonic path length. Experiments have shown that choosing the correct sound pipe length to within a few mils may increase the signal at the receiver by about 20 dB thereby increasing the threshold level or noise immunity. Optimum results are achieved when the sound pipe lengths are equal to an integral number of half wavelengths whereby the sound pipes and feed tube containing a liquid together provide a resonant ultrasonic effect. FIG. 9 shows the resulting partial standing wave pattern in the sound pipes and within the feeding tube at optimum conditions and with no air bubbles present. Best results are obtained when the operating frequency is adjusted so that the feed tube diameter is one-half a multiple of wavelengths $\lambda 2$ in water. [i.e. $D = (m\lambda 2/2)$; where $m$ = some integer, not 0.] At this frequency, sound pipe segments are chosen so that the total distance between receiver and transmit transducer faces, L, is equal to: $L = (n\lambda 1/2) + D$; where $n$ = some integer and $\lambda 1$ is the wavelength in the sound pipe segments at the operating frequency. It is generally unnecessary to optimize all the above conditions precisely to obtain a high received signal: by design, the coupling from transmitter to receiver transducer is good and cavity losses are normally small.

Another feature of the design shown is to choose a sound pipe material having very high acoustic velocity compared to water or the tubing material (generally polyvinyl), resulting in a refractive index of at least 3. Applying the lens formula for a single cylindrical surface [Fundamentals of Optics, Francis A. Jenkins, Harvey E. White, 1957, McGraw Hill, N.Y., (p. 32)] it can be shown that a planar field incident from either sound pipe into the feed tube is focussed to a point at a distance (3R/2) from the incident wave pipe-feed tube interface, where R is one-half the tubing diameter (or its radius). Since ultrasonic energy is normally travelling in two directions within the pipes and the tubing (i.e. from transmitter to receiver and from receiver to transmitter, by reflection), the net effect of this refractive focussing at each cylindrical interface is to cause the standing-wave beam outline to converge toward the center of the tubing, as is shown in FIG. 9. Thus, practically all of the energy passes through the liquid therein, and little passes through the tubing walls. This resonant cavity is similar to a laser tube operating with sperical mirrors. As in the optical case, resonance in this cavity is sensitive to slight losses therein, such as by an air bubble, due to mechanisms already described. Once resonance ceases due to the presence of an air bubble, little energy reaches the receiver transducer, since most of its signal was dependent on the large standing wave.

Referring again to FIG. 5, there is shown, in addition to the transmitter 10 and the sensor head 12, a receiver-detector circuit 50 which comprises an amplifier 52, threshold circuit 54, and a comparator 56. The amplifier 52 comprises transistor Q2 and has a tuned input and an untuned output. the gain of the amplifier is determined primarily by the ratio of the resistors R2 and R3. The gain at 1 megahertz may be designed to be approximately 15. Capacitor C5 is provided to insure that no RF leakage from the transmitter is coupled to the receiver through the battery B1. The receiver should be preferably RF-shielded against pickup from the transmitter. Capacitor C6 and C7 and diodes D1 and D2 form a doubler-peak-detector to extract the peak-to-peak envelope of the signal coupled from transducer 13. Potentiometer P5 may be necessary for adjusting the threshold of detection. The moveable contact of potentiometer P5 couples to one input of comparator 56 which is a conventional comparator readily available to one skilled in the art.

The comparator 56 along with threshold network 54 provide a threshold detector with a small amount of hystersis to assure a positive latching effect without oscillations. The reference voltage provided at the second input to comparator 56 is approximately -600 millivolts. This voltage is provided primarily by diode D4 which is a silicon diode. When the voltage at the negative input terminal to comparator 46 goes more positive than about -570 millivolts, the output of comparator 56 causes current to be drawn by way of light emitting diode (LED) D3 thereby indicating that a bubble has caused the detected RF signal to decrease in magnitude. Potentiometer P5 can control the minimum bubble size that will be detected although generally even a bubble of about one millimeter diameter will drop the received signal by a factor of 30 to 40 times. A large bubble causes a greater drop in the detector signal.

In one experiment the voltage levels at the receiving transducer were measured. With a driving signal at the transmitter end of about eight volts peak-to-peak, and with no bubble being detected there was approximately an 80 millivolt signal detected at the receiving transducer. When a bubble was present this 80 millivolt signal decreased to approximately 1 millivolt.

It is to be understood that the arrangements shown are only one way of constructing a device in accordance with the present invention. For example, the transmitter need not be a sinewave oscillator. It may be a squarewave generator designed to draw a small amount of current at a relatively low voltage. In that case there would not be a requirement for coils L1 and L2 shown in the circuit diagram. Also, any type of a comparator or operational amplifier can be used in the receiver detector ciruit. Also, the comparator could be replaced by a single Darlington transistor. Also, in the drawing, shown in FIG. 5 the indicating means is provided by the light emitting diode D3. obviously, other indicating means could be readily substituted therefore or used in conjunction therewith.

FIG. 6 shows another arrangement of the present invention and specifically depicts a feeding tube 60 and sound pipes 62 and 64 each having associated therewith transducers 63 and 65. The sound pipes 62 and 64 differ from those discussed previously in that their facing ends are fanned out to provide respective elongated channels 67 and 68. For some applications it is desirable to detect only large air bubbles and for that case the arrangement of FIG. 6 is more suitable. In FIG. 6 the sound pipes are shown separated from the feed tube. However, obviously, when in operation the sound pipes would be secured adjacent to the tube similar to the manner shown in FIG. 3. FIG. 7 is another embodiment of the invention wherein the sensor head is to be disposed remote from the circuitry associated with the device. In this arrangement, a cable 70 is provided having a plurality of wires 71 coupling to transducers 73 and 74 one of which is a transmitting transducer and the other of which is a receiving transducer. FIG. 7 also shows the sound absorbent members 75 and 76, hinge member 78 and a holding clip 80. With this arrangment, it is quite easy for the sensor head to be fastened about the feed tube 82 and removed therefrom. The detection of a bubble causes a change in the signal fed by way of cable 70 to a remote central control area where this hazardous condition is monitored.

In accordance with this invention there is also provided, as shown in FIG. 8, a means responsive to detection of an attenuated signal for impeding further fluid flow in the feed tube. FIG. 8 specifically shows a shut-off mechanism 86 which is fastened about an IV tube 87. The mechanism 86 includes an arcuate spring 88 having a pinch member 89 secured to the bottom thereof and adjacent a bottom hump 90 of the mechanism. in FIG. 8 the mechanism is shown in its non-pinching position wherein the coil 91 is not energized, the magnetic slug 92 is withdrawn with the assistance of spring 93, and the arm 94 is engaging with hook member 95 which is also secured to a top surface of the spring 88 opposite to the pinching member 89. The hook member 95 is cocked to this position manually by means of pressure applied against surface 96 with a finger, as shown in FIG. 9. When a detection occurs an output is generated, such as the one generated from comparator 56 in FIG. 5, the coil is energized, the magnetic slug 92 is drawn towards the coil, and the arm 94 disengages from the hook member 95 permitting the IV tube to be pinched between pinch member 89 and hump 90.

When a hazard has been detected and the problem rectified the feeding of fluid through the tube 87 can commence again simply by recocking the spring 88 so that the hook member 95 engages with arm 94.

Figure 10:
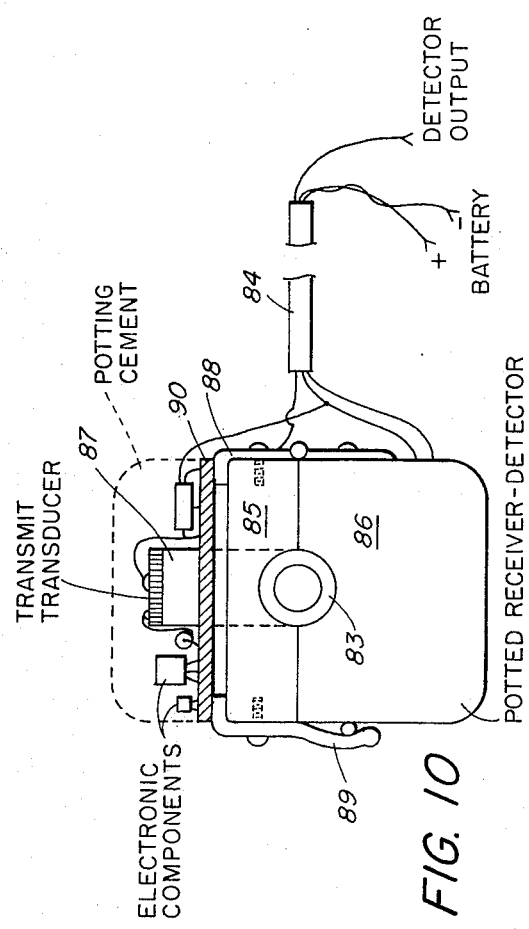
FIG. 10 is a preferred remote sensor.

FIG. 10 is another embodiment of the invention wherein the sensor head is disposed remote from the battery and threshold detector circuitry associated with the device, but includes all other necessary circuitry embedded in itself. In this arrangement, a cable 84 is provided for a single voltage power supply, and an additional lead carries the output of the receiver detector which is referenced to the minus battery lead (or ground). This embodiment allows transmission of preferably only low frequency data (i.e. detected output) and D.C., but does not require any high level or low level RF transmission. Transmission of RF requires coaxial cables, special drive circuitry, and is subject to interference, noise, and stray pickup. In this embodiment shown in FIG. 10 stray pickup, noise, and interference are minimized by low-pass filtering the battery leads at the remote sensor head (see capacitors C4 and C5 in FIG. 5) as well as at the main circuitry containing the threshold comparator. No coaxial transmission cables are thus necessary, as any set of three twisted wires will suffice.

In the embodiment shown in FIG. 10, each sound absorbent half-cube 85 and 86 is reduced in size, but made sifficiently large to still hold the sound pipes tightly in position. Only pipe 87 is shown in FIG. 10. A metal hinge 88 and holding clip 89 are included and held by fasting screws, as shown. At least one fastening screw is used as a battery ground potential connecting point for both receiver and transmitter sections, and also serve to recess the transmitter and receiver printed circuit boards, as shown. The transmit circuit board 90 includes all the components shown in FIG. 5 in transmitter 10. The receiver-detector circuit board not shown in FIG. 10 includes the preamplifier Q2, associated components and the peak detector which includes capacitors C6 and C8 and diodes D1 and D2. Each board is square and contains a center hole to clear the sound pipe without direct contact therebetween. The position of the transmitter and receiver-detector circuitry as shown in the embodiment assures minimum electromagnetic coupling between them and requires no RF shielding. In this arrangement it is quite easy for the sensor head to be fastened about the feed tube 83 and removed therefrom. The detection of a bubble causes a decrease in the detected signal amplitude fed by way of cable 84 to a central control device which compares the signal with a predetermined threshold level, signalling the hazardous condition. The present invention disclosed herein illustrates a limited number of embodiments. It is contemplated that numerous other embodiments and modifications thereof should fall within the spirit and scope of the present invention.

What is claimed is:

1. An ultrasonic through-transmission bubble detector for use with a hollow, flexible tube for feeding liquid and comprising:
   a first sound coupling element arranged on one side of the tube and having one end defining a concave lensing surface contacting the tube;
   transducer means coupled to the other end of said first sound element;
   means applying a signal to said transducer means for causing said transducer means to establish a collimated ultrasonic signal in the first sound element;
   a second sound coupling element arranged on the opposite side of the tube to the first sound element to unidirectionally receive the ultrasonic signal transmitted through the tube and the liquid disposed in the internal space defined by the tube;
   said second sound coupling element having one end defining a concave lensing surface contacting the tube;
   said first and second element lensing surfaces extending about a major circumference of the tube but defining a gap between the facing element ends;
   the total gap circumference being less than the lensing surface circumference;
   said first and second sound coupling elements both being constructed of a material having a greater acoustic velocity than that of the liquid or tube to provide a first refractive index between the first sound coupling element and tube greater than unity at the lensing surface of the first element, and a second reciprocal refractive index between the tube and second sound coupling element at the lensing surface of the second element;
   said lensing surfaces and said material in combination providing a lensing effect, respectively, whereby the beam pattern of the ultrasonic signal is converged inside the tube and collimating the ultrasonic signal with the minimum width of the beam pattern inside the tube being less than the inner diameter of the tube;
   and means coupled from the second sound element for receiving the collimated ultrasonic signal including means for establishing an alarm condition.

2. The detector of claim 1 including first and second sound absorbent members having said first and second sound elements respectively imbedded therein.

3. The detector of claim 2 wherein each sound element includes a sound pipe.

4. The detector of claim 3 including means for securing the sound pipes against the tube.

5. The detector of claim 4 wherein the facing concave ends are arcuate for accommodating the tube.

6. The detector of claim 3 wherein each sound pipe has a length that is an integral number of half wavelengths of the material of which it is constructed.

7. The detector of claim 1 wherein the means applying the signal includes an oscillator circuit and the transducer means includes a transmitting transducer coupled to the first sound element.

8. The detector of claim 6 wherein the receiving means includes amplifier means, means for establishing a threshold level and comparator means coupled from the amplifier means and responsive to the received signal falling below the threshold level for enabling an alarm means.

9. The detector of claim 3 wherein the feed tube has a diameter that is an integral number of half wavelengths of the fluid flowing in the tube.

10. The detector of claim 3 wherein the total distance (L) between opposite ends of the sound pipes is equal to the diameter of the tube plus an integral number of half wavelengths of the material of which it is constructed.

11. A detector as set forth in claim 1 wherein the ends of the sound elements are substantially the same size as or larger than the diameter or like cross-dimension of the tube.

12. A detector as set forth in claim 1 wherein the concave ends are at least partially of a shape coincident with the shape of the tube.

13. A detector as set forth in claim 12 wherein the concave ends have an arcuate curvature to match a circular tube.

14. An ultrasonic through-transmission bubble detector for use with a hollow tube for feeding a liquid, said detector comprising; a pair of sound conductors disposed on opposite sides of said tube, each said conductor having one end defining a concave leensing surface, means for maintaining said conductors lensing surfaces intimately in contact with said tube, means coupled to one of said sound conductors for establishing an ultrasonic signal in the one conductor, and means coupled from the other sound conductor for receiving the ultrasonic signal, the facing lensing surfaces of said conductors being arranged to surround a major circumference of the tube with a gap defined between the facing conductor ends when so intimately coupled to the tube and establish a standing wave pattern in the conductors and liquid in the tube, which standing wave pattern is interrupted upon passage of a bubble, said conductors both being constructed of a material having a greater acoustic velocity than that of the liquid or tube said lensing surface of the one conductor and said material in combination converges the ultrasonic signal toward the center of the tube and the lensing surface of the other conductor and said material in combination collimates the beam back to the other conductor, with the minimum width of the standing wave beam pattern inside the tube being less than the inner diameter of the tube.

15. The detector of claim 14 including a pair of sound absorbent members, one associated with each sound conductor at least partially for confining the signal to the sound conductors.

16. The detector of claim 14 wherein the total distance between opposite remote ends of the conductors is equal to the diameter of the tube plus an integral number of half wavelengths of the material of which it is constructed in order to sustain the standing wave pattern in the absence of a bubble.

17. The detector of claim 14 wherein each sound conductor has a higher index of refraction than the tube.

18. The detector of claim 17 wherein the incident wave from the one conductor is focused to a point at a distance of approximately 3R/2 from the point where the one conductor and tube join.

19. The detector of claim 14 wherein the lensing surfaces of both conductors extend about the tube over a total circumference greater than half the circumference of the tube.

* * * * *